US005454043A

United States Patent [19]

Freeman

[11] Patent Number: 5,454,043

[45] Date of Patent: Sep. 26, 1995

[54] DYNAMIC AND STATIC HAND GESTURE RECOGNITION THROUGH LOW-LEVEL IMAGE ANALYSIS

[75] Inventor: William T. Freeman, Newton, Mass.

[73] Assignee: Mitsubishi Electric Research Laboratories, Inc., Cambridge, Mass.

[21] Appl. No.: 99,944

[22] Filed: Jul. 30, 1993

[51] Int. Cl.$^6$ .............................. G06K 9/00; G09G 1/06; A06F 15/62

[52] U.S. Cl. .......................... 382/168; 382/170; 345/122; 395/199; 395/155

[58] Field of Search .................................. 382/18, 1, 16, 382/51; 358/105, 125, 126; 348/169, 214, 578, 700; 395/152, 155, 119, 161, 100; 345/122, 158

[56] References Cited

U.S. PATENT DOCUMENTS

| | | | |
|---|---|---|---|
| 4,542,657 | 9/1985 | Barber et al. | 73/861.25 |
| 4,567,610 | 1/1986 | McConnell | 382/18 |
| 5,010,500 | 4/1991 | Makkuni et al. | 364/521 |
| 5,047,952 | 9/1991 | Kramer et al. | 364/513.5 |
| 5,138,671 | 8/1992 | Yokoyama | 382/51 |
| 5,203,704 | 4/1993 | McCloud | 434/156 |
| 5,214,615 | 5/1993 | Bauer | 367/128 |
| 5,227,985 | 6/1993 | DeMenthon | 364/559 |
| 5,243,418 | 9/1993 | Kuno et al. | 358/126 |

OTHER PUBLICATIONS

Magenes, Giovanni, et al., "Hand Movement Strategies in Telecontrolled Motion Along 2–D Trajectories", IEEE, Mar. 1992, pp. 242–257.

*Primary Examiner*—Leo H. Boudreau
*Assistant Examiner*—Matthew C. Bella
*Attorney, Agent, or Firm*—Robert K. Tendler

[57] ABSTRACT

A low-level model-free dynamic and static hand gesture recognition system utilizes either a 1-D histogram of frequency of occurrence vs. spatial orientation angle for static gestures or a 2-D histogram of frequency of occurrence vs. space-time orientation for dynamic gestures. In each case the histogram constitutes the signature of the gesture which is used for gesture recognition. For moving gesture detection, a 3-D space-time orientation map is merged or converted into the 2-D space-time orientation histogram which graphs frequency of occurrence vs. both orientation and movement. It is against this representation or template that an incoming moving gesture is matched.

7 Claims, 7 Drawing Sheets

DYNAMIC AND STATIC HAND GESTURE RECOGNITION THROUGH LOW-LEVEL IMAGE ANALYSIS

FIELD OF INVENTION

This invention relates to computer interfaces and more particularly to gesture recognition for computer control.

BACKGROUND OF THE INVENTION

As will be appreciated, there are a variety of computer interface devices for control by hand namely, the mouse, the pen, the joystick, the trackball, and more recently, the data glove. While these devices are presently satisfactory for many applications, some systems require more flexibility for convenient computer control.

By way of example, data gloves which fit over the human hand with an umbilical line to the computer control the motion of icons such as flying figures which move through a virtual reality scene. The use of such a data glove is both cumbersome and expensive in view of the numbers of internal sensors within the data glove and the trouble of having to take it on and off. As a result, researchers have searched for computer control systems which are not so hardware dependent. Gesture recognition is one such class of systems.

The detection of gestures is important because not only does the orientation of the hand give valuable information, so does hand movement. Thus, while a thumbs up static gesture may indicate approval, this same gesture when moving can indicate "thumbing" or the request for a ride. Likewise, although the attitude of a hand is detectable, it is the detection of its dynamic movement which more accurately defines the gesture.

In the past, as reported in the March 1992 IEEE conference proceedings, IEEE catalog number 92CH3168-2, entitled "Recognizing Human Action In Time Sequential Images Using Hidden Markov Model" by Yamato, Ohya and Ishii of the NTT Human Interface Laboratories in Yokosuka, Japan, a hand gesture recognition system is described that takes static pictures of some action and utilizes the Hidden Markov Model to infer which of a set of possible gestures a given video input corresponds to. However, such an approach, which was originally developed for speech recognition purposes, can be computationally intense. Another problem with respect to this approach to gesture recognition is that it measures motion only inferentially. This is due to the fact that motion between various of the pictures is never represented or calculated.

As described in a paper delivered at the Imagina '93 Conference entitled "A Human Motion Image Synthesizing By Model-Based Recognition From Stereo Images" authored by Ishii, Mochizuki and Kishino, another approach to vision-based hand gesture recognition employs a stereo camera method. Here a model of the human figure is employed, with the model being fit to stereo range data in order to infer the angles between the joints and therefore the orientation of the arm or hand.

The most serious problem with such a system is that it is model based in that if one wishes to have this work on other than a human figure, a new model must be introduced. As will be appreciated, this system is not a "low level" system because it relies on high level models in the recognition process.

Additionally, as described in MIT Media Laboratory Vision And Modeling Group Technical Report No. 197 entitled "Recognition of Space Time Gestures Using a Distributed Representation" by Trevor J. Darrell and Alex P. Pentland, gestures are detected from a series of templates, not unlike a series of pictures. Gestures are identified in this system by a sequence of static hand positions, where a particular hand position is determined by taking the template and convolving it with the entire image to find the best fit. Even though this technique offers a so-called "low level" approach because high level models are not used, the Darrell/Pentland technique is even more computationally intensive than the above-mentioned Yamato-Ohya-Ishii system due to the need for convolution with large masks. Also, being intensity-based, this system is not particularly robust for changes of lighting, and like the other systems described above, does not measure motion directly but rather analyzes a sequence of static poses.

By way of further background, it will be appreciated that so-called "orientation histograms" have been utilized for texture analysis. This work is described by Mojgan Monika Gorkani of the MIT Media Laboratory, published in the MIT Media Laboratory Perceptual Computing Group Technical Report, No. 222, May, 1993. In this paper, orientation histograms are developed for the purpose of analyzing "textures" by looking at local peaks in the orientation histogram. However, detecting only histogram peaks throws out or destroys certain relevant information which is useful in analyzing static or dynamic gestures.

As an application for gesture recognition, recently, there has been interest generated in so-called teleconferencing. In teleconferencing, rather than transmitting full frame video, various scenarios are depicted at the teleconferencing site. What is actually shown to the teleconference participants is determined by, for instance, hand gestures or head gestures, or a combination of both. Such a system is described in IEEE Transactions on Pattern Analysis of Machine Intelligence, Volume 15, No. 6, June 1993, in an article entitled "Visually Controlled Graphics" by A. Azarbayejani, T. Starner, B. Horowitz, and A. Pentland. In this system corner points are detected as the features of interest, with the corners then being tracked in space and time to determine head position. It will be appreciated that this system is not particularly well adapted to articulated objects, like the human hand.

In summary, most hand-controlled human-computer interface devices have severe limitations. The mouse, the pen and the trackball only give two-dimensional position information. Also, the joystick only gives information about two angles. All these methods require physical hardware for the hand to hold, which is cumbersome to have to carry, pick-up or grasp.

In an effort to get away from physical hardware, model-based visual methods for recognizing hand gestures have been developed, but tend to be slow, because there are many possible ways a hand could be fitted to the visual data. Furthermore, model-based methods require the generation of a new model, and potentially a redesign of the entire algorithm in order to extend the work to analyze non-hand inputs.

It will be appreciated that what people perceive as a gesture is not simply a series of static snapshot type poses of a particular object, such as a hand, but rather what is perceived is the motion of the hand between these static poses. Thus while a system which tries to measure gestures may incorporate the static snapshots of the object as it goes through its motion, it should also describe or recognize the motion itself. Since none of the above systems measure motion directly, they are incapable of the type of gesture recognition which is required.

SUMMARY OF THE INVENTION

In order to recognize gestures, in the Subject System the task is broken down into two components, the static and the dynamic. First, in order to analyze the static component, the Subject System analyzes the visual image based on local spatial orientation in the image. For instance, for recognizing static hand position, the distribution of spatial orientations over the image is detected and a spatial orientation map is generated. From the spatial orientation map, a characteristic "signature vector" is derived which characterizes the particular hand position. In one embodiment, the signature vector is a 1-D histogram of the frequency with which each particular orientation occurs in the image graphed against orientation or angle. This is a low level approach because no model of the gesturing object is required.

It will be appreciated for static image analysis that this 1-D histogram is a histogram over space as opposed to over time. This means that what is detected is the set of orientations of the object as they occur in particular positions in space. More specifically, the static case histogram is a graph of frequency of occurrence versus orientation or angle, and it is this histogram which forms the signature for static gesture recognition. In one embodiment, this signature is intentionally blurred by convolution with a low pass filter to provide a smooth signature for signature matching purposes.

Once having derived this low-level image signature, one can compare a signature derived from an actual video camera output with a stored set of signatures. Closest match or curve-fitting techniques are utilized to determine which of the stored signatures has the closest match to the signature of the incoming video signal to identify the hand pose or the static gesture. Even so, static gesture recognition alone may not be sufficient for gesture recognition.

When a gesture is more than just a frozen orientation, motion must also be detected. This motion is directly measured in the Subject System by first deriving a 3-D space, time, orientation map. This map is a 3-D plot of spatio-temporal orientations as a function of space and time. Definitionally, this is a plot in 3-D space-time of unit vectors oriented in the direction of the local spario-temporal image intensity gradient. The spatio-temporal image intensity gradients are found by taking derivatives of the image intensity as a function of horizontal, vertical and temporal position.

It is this 3-D map which is converted into a 2-D histogram or template for dynamic gesture matching.

As will be seen the 2-D template combines orientation with movement to characterize a gesture. For instance, a 2-D space-time orientation histogram or template of a thumbing gesture would be an eyebrow curve, with the beginning of the eyebrow starting at zero movement with a stationary thumb at 0°. As the thumb moves to the right the eyebrow curve goes up indicating movement to the right. The eyebrow curve goes down as the thumb ends up stationary at 90°. This 2-D template signature thus uniquely defines the usual thumbing motion.

It will be appreciated that this template is the reference for a moving gesture to which other moving gestures are matched. Thus orientation and movement are accounted for in one template. This technique involving a 3-D space-time-orientation map converted to a 2-D space-time orientation histogram, while being somewhat more computationally intensive than the static low level system described for static images, is easily implemented through well known image processing techniques to provide a unique measure of gesturing.

Note, the subject gesture recognition system while initially achievable through a novel static histogram technique, is improved through the measurement of motion directly through the utilization of 2-D space-time orientation histograms.

Note also that one could average the 2-D space-time orientation histogram of a particular gesture over several different users in order to obtain a space-time orientation histogram reference which is substantially user independent.

In one embodiment for deriving static orientations, spatial filtering provides the x derivative and the y derivative of the video input signal, with the arc tangent of the pair being taken to obtain the spatial orientation. This output may optionally be multiplied by two, and wrapped to zero and 360°. Here, the multiplier and the wrapping are optional to convert the angle measurement to the sign of contrast-independent orientation measurements. However, in some cases, the sign of contrast dependent orientation measurements are sufficient. The arc tangent operation provides the angle of the object, whereas contrast strength is achieved by taking the x and y derivatives and summing their squares. It will be appreciated that contrast strength may be utilized as a threshhold so that angles or orientations having a strength below a certain threshhold are ignored. This is useful in cancelling low-contrast noise in the area surrounding the object.

Having derived the static case histogram as being one of the frequency of occurrence versus orientation, the utilization of the aforementioned blurring technique permits recognition of an angle which is slightly off. This technique provides a process by which angles which are close are detected as one angle, versus an angle which is clearly different.

In terms of recognizing dynamic gesturing, an image is initially digitized as a sequence, followed by low pass spatial filtering and then x, y and z derivatives. This set of derivatives is utilized to compute the spatio-temporal orientation, with the derivatives also utilized to compute contrast strength, thereby to compute the space-time-orientation map. The 3-D space-time-orientation map is then converted to a 2-D space-time orientation histogram by recording, for each possible spatio-temporal orientation represented in the space-time orientation histogram, the number of occurrences of that orientation in the space-time orientation map.

This histogram may optionally be blurred for the reasons noted above. The output after blurring is then applied to a local gain control to assure that small regions of the image are not swamped by the large regions. This permits recognition of small but characteristic motions which are useful identifiers for a gesture. The output after local gain control is the signature of the dynamic gesture.

Thus the subject dynamic and static hand gesture recognition system for computer control utilizes either a spatial orientation histogram for static images, or a space-time orientation histogram for dynamic gesture recognition. Typically, orientation signatures are derived in a training sequence for a number of different hand positions. Thereafter, a run time algorithm detects a digitized version of the video hand image and directs the requested computer action in accordance with detected hand pose or configuration. Both static and dynamic actions are recognized, with the system capable of detecting normal human hand movement to indicate, for instance, "turn around", "go to the left", or "hello". Static gestures include placing the hand at a particular orientation, with the computer ascertaining the angles describing that orientation.

The system is also capable of recognizing or classifying other visual inputs as well, including, for example, detecting people walking in a video. Applications for more general low-level visual analysis include surveillance, and content-based access to multi-media databases, in which a database can be queried for moving or static images of a predetermined type.

The advantages with the present approach to gesture recognition are first, that the signature vectors are based on local orientation, which is relatively robust to chages in lighting. Secondly, the signature vectors are easy and fast to compute. Additionally, the Subject System is a low-level system and therefore can be used to analyze inputs other than just hand gestures. Finally, the dynamic gesture recognition directly measures motion because it includes motion information contained in the signature vector. This yields gesture characterizations which are in agreement with human perceptual characterizations.

BRIEF DESCRIPTION OF THE DRAWINGS

These and other features of the Subject Invention will be better understood taken in conjunction with the Detailed Description in conjunction with the Drawings of which.

DETAILED DESCRIPTION

Figure 1:
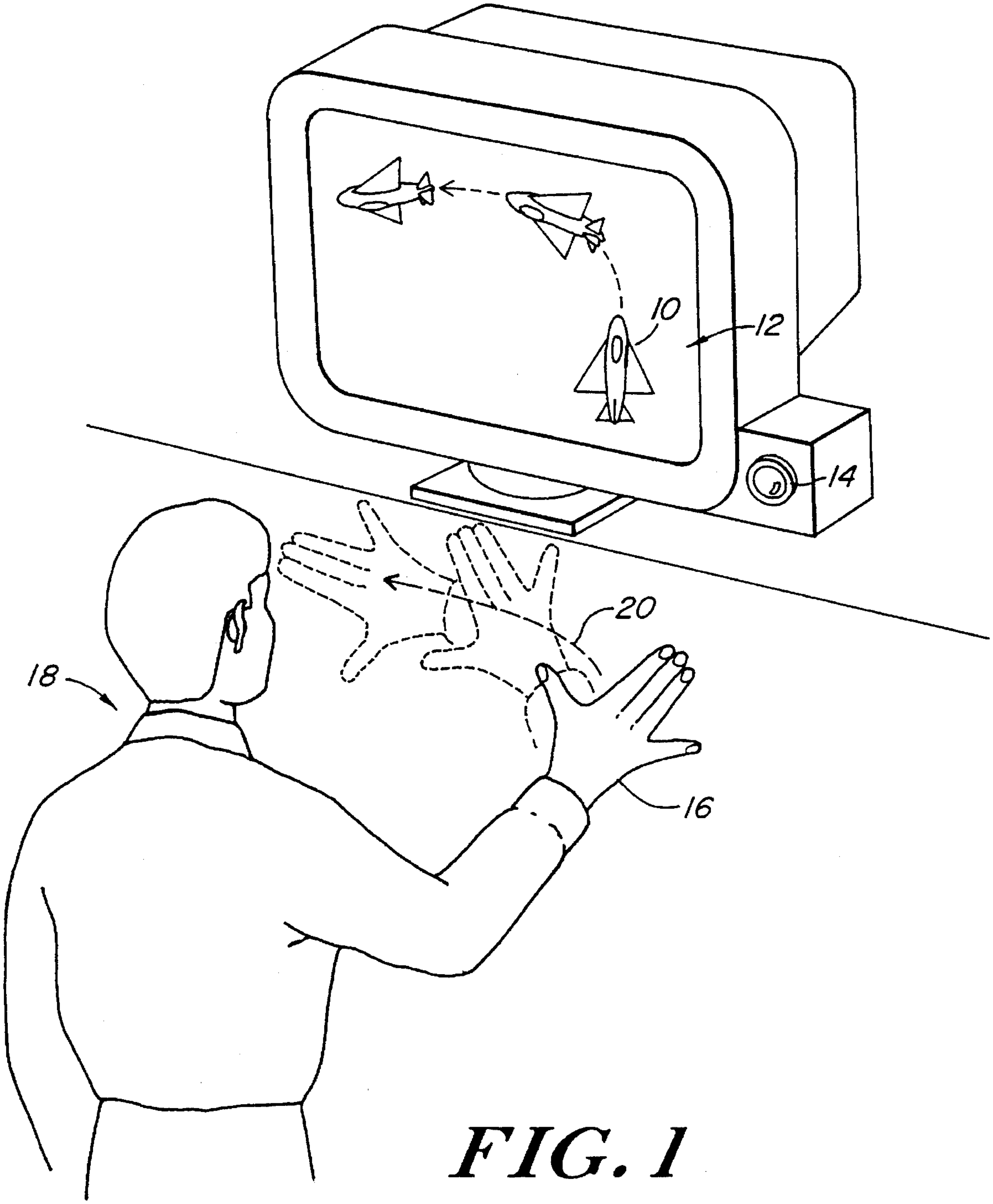
FIG. 1 is a diagrammatic representation of dynamic gesture recognition for the control of a moveable icon on a CRT or display.

Referring now to FIG. 1, it is important for the control of icon 10 displayed at a display 12, that the position of the icon be determined not by hardware operated inputs but rather through gesture recognition in which a video camera 14 scans the hand 16 of an individual 18 in order to determine what the icon should do or more generally what the computer action should be upon hand signal recognition.

As illustrated, the hand is moved in a dotted path 20 to simulate the flight of an airplane, with icon 10 being controlled by virtue of scanning the hand and providing a digital image thereof for processing. For dynamic gesture recognition the processing, as will be seen, includes an algorithm which generates a 2-D template which is utilized as a low-level system to detect various moving gestures.

Figure 2A:
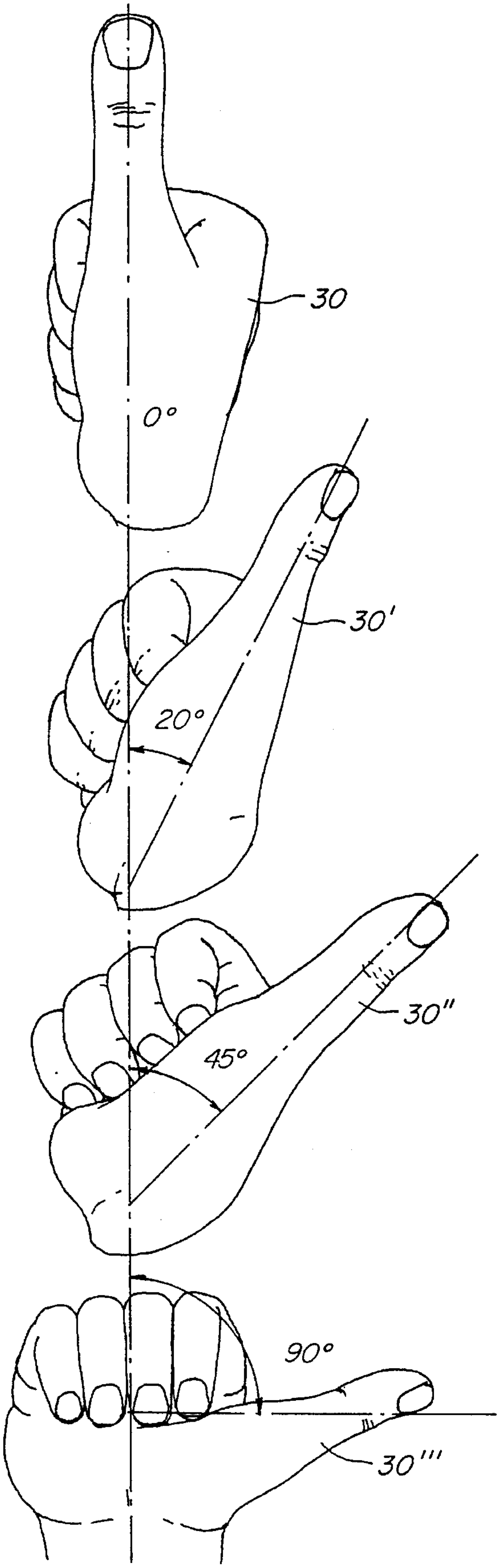
FIG. 2A is a diagrammatic representation of a thumbing gesture in one of a number of angular orientations of the thumb.

Prior to describing static gesture recognition which is a part of the dymanic gesture recognition system, it will be appreciated in connection with FIG. 2A that a thumbing gesture, here shown by thumb 30, can be characterized in terms of the angle that the thumb makes with the vertical. As can be seen, at the start of a thumbing gesture the thumb is in a vertical position at 0°. Thereafter as illustrated at 30', the thumb is moved to 20°, whereas as shown at 30", the thumb moves through 45°, then coming to rest as shown at 30''' at 90°. It will be appreciated that the tip of the thumb is in fact moving to the right. Of course, in normal thumbing gestures the arm as well as the thumb is moving to the right.

What will be appreciated is that rather than a static gesture of an upwardly pointing thumb indicating, for instance, approval, or downwardly pointing thumb indicating, for instance, disapproval, the Subject System is capable of recognizing a moving gesture in which in this case the thumb has moved from a vertical position to a horizontal position, but is also moving in time from one position to the other.

Figure 2B:
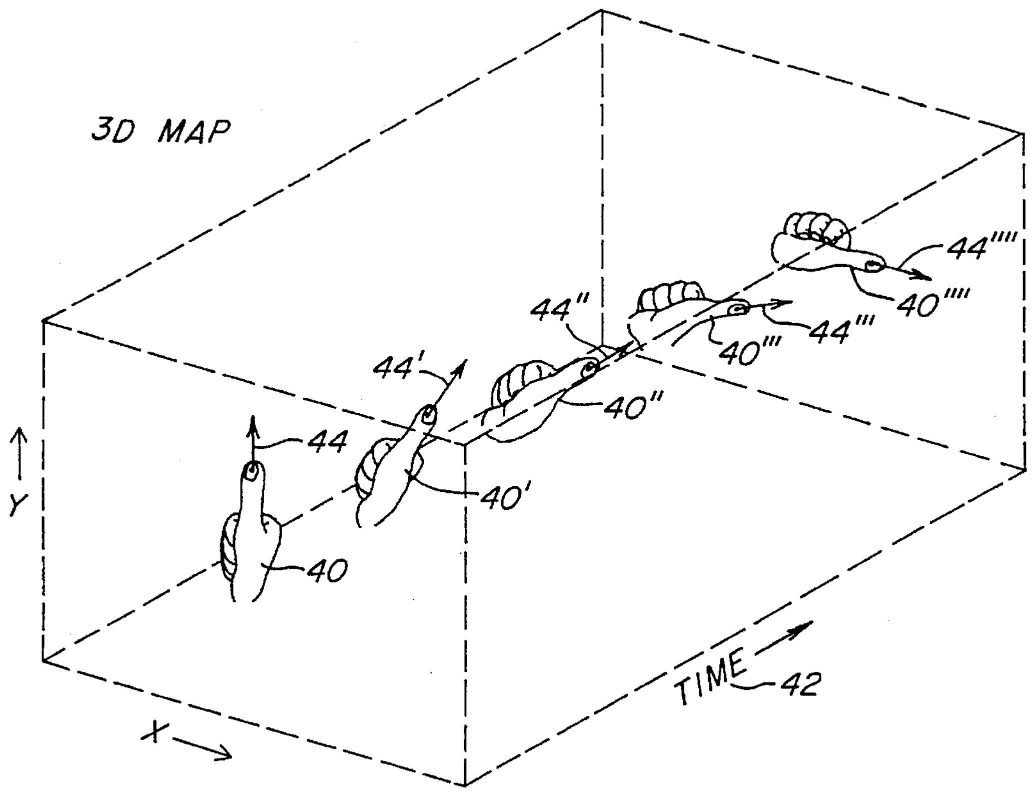
FIG. 2B is a diagrammatic representation of a 3-D space-time-orientation map of the thumb during the thumbing gesture of FIG. 2A.

In the Subject System this is captured by a system which generates a 3-D map, as illustrated at FIG. 2B, which in essence captures the digital image 40 at various time positions 40', 40", etc., with the positions being on the time axis 42 as illustrated. As will be seen, unit vectors 44 have their origins at the tip of the thumb, and are oriented in the dominant direction of the thumb over time. Thus as can be seen for the dynamic gesture recognition of a thumbing gesture, the orientation of vectors 44 rotate to the right as would be appropriate in tracking the dominant direction of the thumb during the thumbing motion.

Figure 2C:
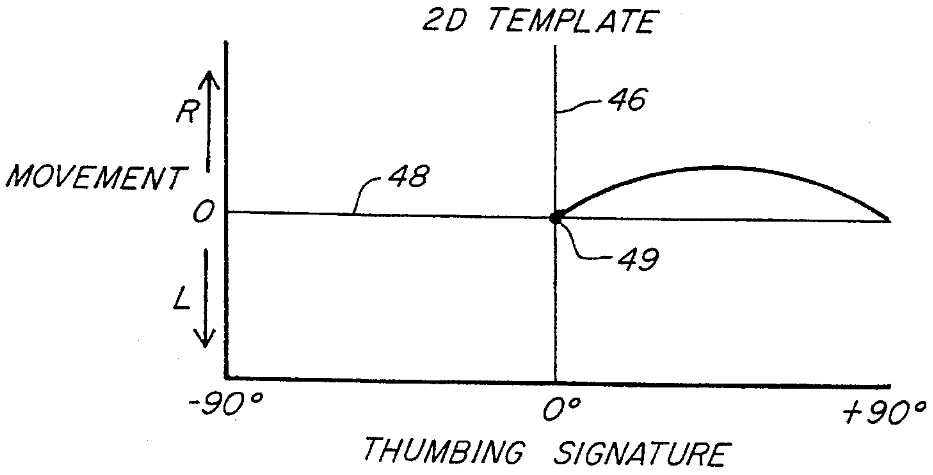
FIG. 2C is a 2-D template illustrating an eyebrow-type curve which is the result of the detection by the Subject System of the thumbing motion illustrated in FIG. 2A.

Once having derived the 3-D map through a technique to be described hereinafter, it is then necessary to convert or merge the 3-D map into a 2-D template or histogram as illustrated in FIG. 2C. As will be described, this can be done conveniently with the above-listed algorithms. For present purposes, it will be noted that the 2-D template graphs spatial orientation against movement. Here, while movement to the left and right is depicted, the graphed movement is more precisely either along the spatial gradient or against the spatial gradient. It will be also appreciated that there is a vertical 0° axis shown at 46 and a horizontal 0° axis shown at 48.

Analyzing the thumbing gesture, it will be appreciated that the thumb is originally at 0° and is not moving at all. This is the origin of the graph as illustrated by point 50. As the thumb rotates from 0° through to 9° the position of occurrences moves out along the horizontal, whereas movement is denoted by a vertical rise in the position of the occurrrences of an angular orientation above horizontal line 48. The generation of the 2-D template is that against which all subsequent movements are matched by typical curve matching techniques.

Figure 3:
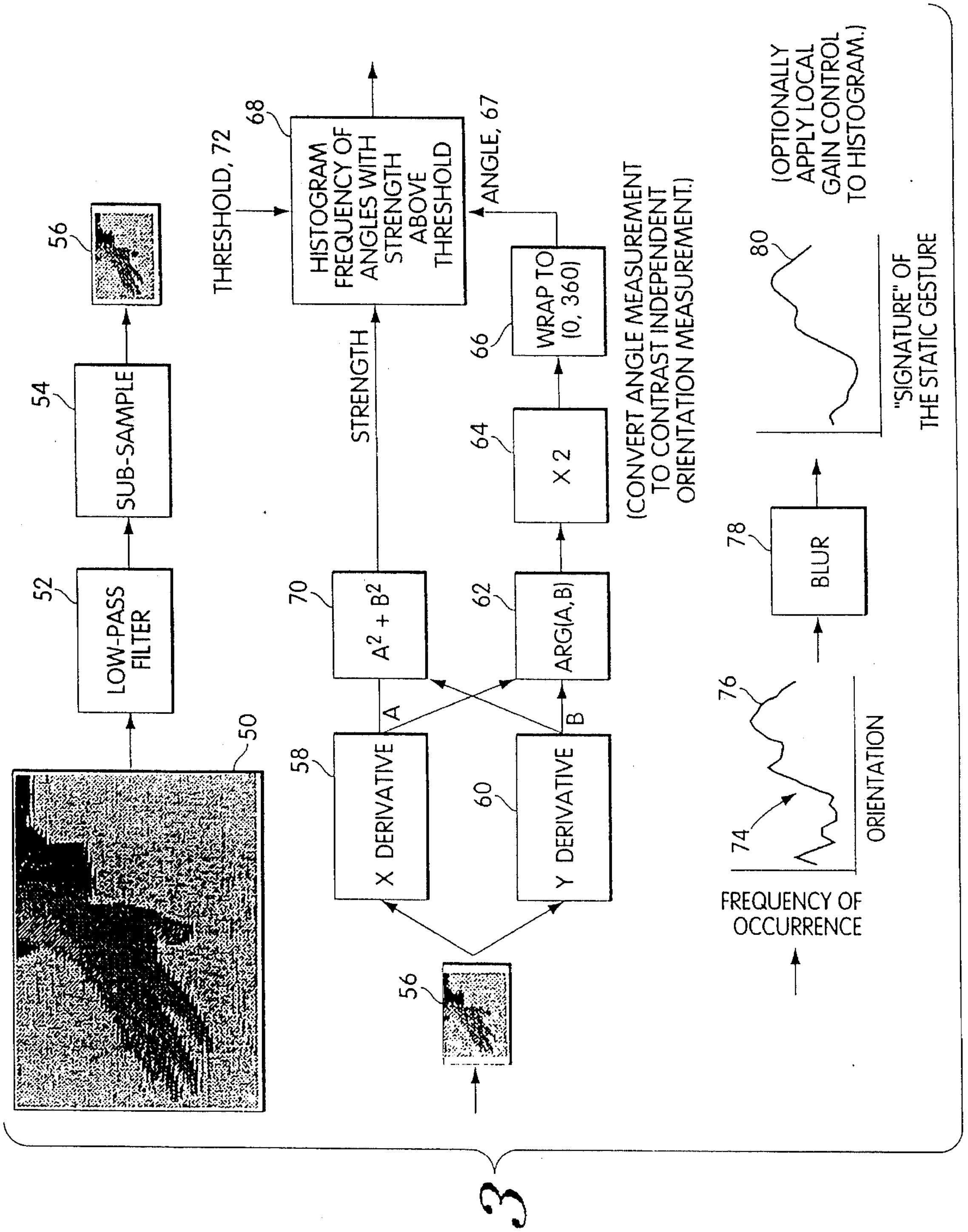
FIG. 3 is a diagrammatic, photographic and schematic diagram illustrating the calculation of the signature vector for a static image from a digitized image of a hand through the formation of a frequency of occurrence vs. orientation histogram which has been optionally smoothed.

Referring now to FIG. 3, the determination of the histogram for the static gesture is described as follows. First, a digitized image 50 of a hand is provided. The image is low pass filtered at 52 and subsampled at 54 to provide a subsampled image 56 as illustrated. The subsampled image is then utilized in the taking of the x derivative and the y derivative as illustrated at 58 and 60, respectively. These two derivatives form the aforementioned gradient spatial intensity. An arc tangent operation is performed at 62 to derive the particular angle 67 which has been detected. Optionally to convert angle measurement to contrast independent orientation measurement, the result is multiplied by two as illustrated at 64 and is wrapped to 0° or 360° as illustrated at 66. The result of this operation is the detection of the dominant angle which is then applied to a unit 68 which provides a histogram of the frequency of occurrence of an angle as a function of angular orientation for all of those data points which are above a given image intensity strength threshhold. The gradient strength is derived as follows.

The outputs of the x and y derivative generating units 58 and 60 are combined in a squaring operation by a squaring unit 70, with the squares indicating the gradient strength of the particular data point in question. The strength is applied to unit 68 with the threshhold 72 being set such that angles corresponding to image intensity gradients under a predetermined threshhold will be ignored.

The output of histogram generator 68 is a graph as illustrated at 74 of the frequency of occurrence of a given angle vs. orientation or angle. This produces a jagged signature 76 which, with conventional blurring 78, produces a smooth signature of the static gesture as illustrated at 80. It will be appreciated that it is also possible to optionally apply local gain control to the histogram.

For static gesture recognition, the spatial intensity gradient from which the histogram is developed is:

$$S_G=\left(\frac{dI}{dx}\right)\hat{x}+\left(\frac{dI}{dy}\right)\hat{y}$$

where $\hat{x}$, $\hat{y}$ are unit vectors in the x and y directions, respectively.

The 1-D histogram is generated as follows:

$$\phi=\arg\left(\frac{dI}{dx},\frac{dI}{dx}\right), \text{ where } \phi=\text{orientation}$$

For dynamic gesture recognition $$\left(\frac{dI}{dt}\right)\hat{t}$$

is added such that the dynamic gesture gradient is $$D_G=\left(\frac{dI}{dx}\right)\hat{x}+\left(\frac{dI}{dy}\right)\hat{y}+\frac{dI}{dt}\hat{t}$$

whose $\hat{t}$ is a unit vector in the temporal direction.

For the 2-D dynamic gesture histogram $$\phi=\arg\left(\frac{dI}{dx},\frac{dI}{dy}\right)$$

$$\theta=\arg\left(\frac{dI}{dt}/a,\frac{b}{a}\right)$$

where

-continued $$a=\sqrt{\left(\frac{dI}{dx}\right)^2+\left(\frac{dI}{dy}\right)^2+\left(\frac{dI}{dt}\right)^2}$$

$$b=\sqrt{\left(\frac{dI}{dx}\right)^2+\left(\frac{dI}{dy}\right)^2}$$

where $\phi$=orientation and $\Theta$=movement.

In general, static gesture analysis starts with a spatial orientation map that one gets when one takes the 2-D gradient and finds the orientation everywhere. From the spatial orientation map, one forms a 1-D spatial orientation histogram by the following algorithm:

1) raster scan the (2-d) spatial orientation map
2) read-out orientation of each vector
3) go to the (1-d) spatial orientation histogram and add "1" to the count value stored at the orientation corresponding to this vector.
4) continue, from step 1, for the whole spatial orientation map.

Note that for static gesture recognition there is a training phase in which static histogram signatures are developed. In one embodiment, the steps involved in the training phase for a static gesture recognition implementation are as follows. First, the computer displays a target orientation indicator usually by crosshairs. Secondly, the individual orients his hand to match the orientation of the target by placing his fingers in the direction of the crosshairs. Thirdly, the computer digitizes the image of the hand and calculates and stores corresponding signature vectors along with target orientation information. Next, the computer displays the next target orientation indicator and the individual orients his hand to the newly oriented crosshairs. Thereafter the computer digitizes the image of the hand and calculates and stores the signature vector target orientation for this particular orientation, with the steps being repeated until such time as the training sequence have a significant number of signatures against which to match incoming information.

In one embodiment, interpolation is used in signature matching. In one embodiment, a common interpolation is used in which the computer calculates and stores the coefficients for the interpolation function. The interpolation function allows fast calculation of orientation as a function of signature vector.

Note that in order to obtain hand orientation as a function of image signature vector one can use any of several well-known interpolation techniques, such as linear interpolation or radial basis functions. In this example, one can use gaussian radial basis functions. Assuming $\phi$=F(v) has the form $$\phi=ae^{-\|v1-v\|^2/2\sigma^2}+be^{-\|v2-v\|^2/2\sigma^2}+ce^{-\|v3-v\|^2/2\sigma^2}$$

One can pick the parameter $\sigma$ by trial and error. A good value to use is the average distance between all the training vectors.

In order to find a, b and c, these can be found by enforcing that the function F yield the known values for for v=the training vectors. For this example, this gives the matrix equation, $$\begin{pmatrix} 10 \\ 20 \\ 30 \end{pmatrix} = \underbrace{\begin{pmatrix} 1 & e^{-\|v_1-v_2\|^2/2\sigma^2} & e^{-\|v_1-v_3\|^2/2\sigma^2} \\ e^{-\|v_1-v_2\|^2/2\sigma^2} & 1 & e^{-\|v_2-v_3\|^2/2\sigma^2} \\ e^{-\|v_1-v_3\|^2/2\sigma^2} & e^{-\|v_2-v_3\|^2/2\sigma^2} & 1 \end{pmatrix}}_{A} \begin{pmatrix} a \\ b \\ c \end{pmatrix}$$

By pre-multiplying both sides of the above equation by the inverse of the matrix A, one can find the desired values of a, b and c.

In the run time phase for static gesture recognition, an individual places his hand at some orientation in view of a camera. The computer digitizes the hand image and converts it to a signature vector. Then the computer calculates orientation of the hand from the interpolation function, which uses the training signature vectors, at their respective orientations and the interpolation coefficients. Next the computer changes the display or operates in some way in response to the calculated values of the hand. For example, it may simulate tilting the aircraft of FIG. 1 to have the orientation of the hand. Finally, all of the steps are repeated for different static gestures.

Figure 4:
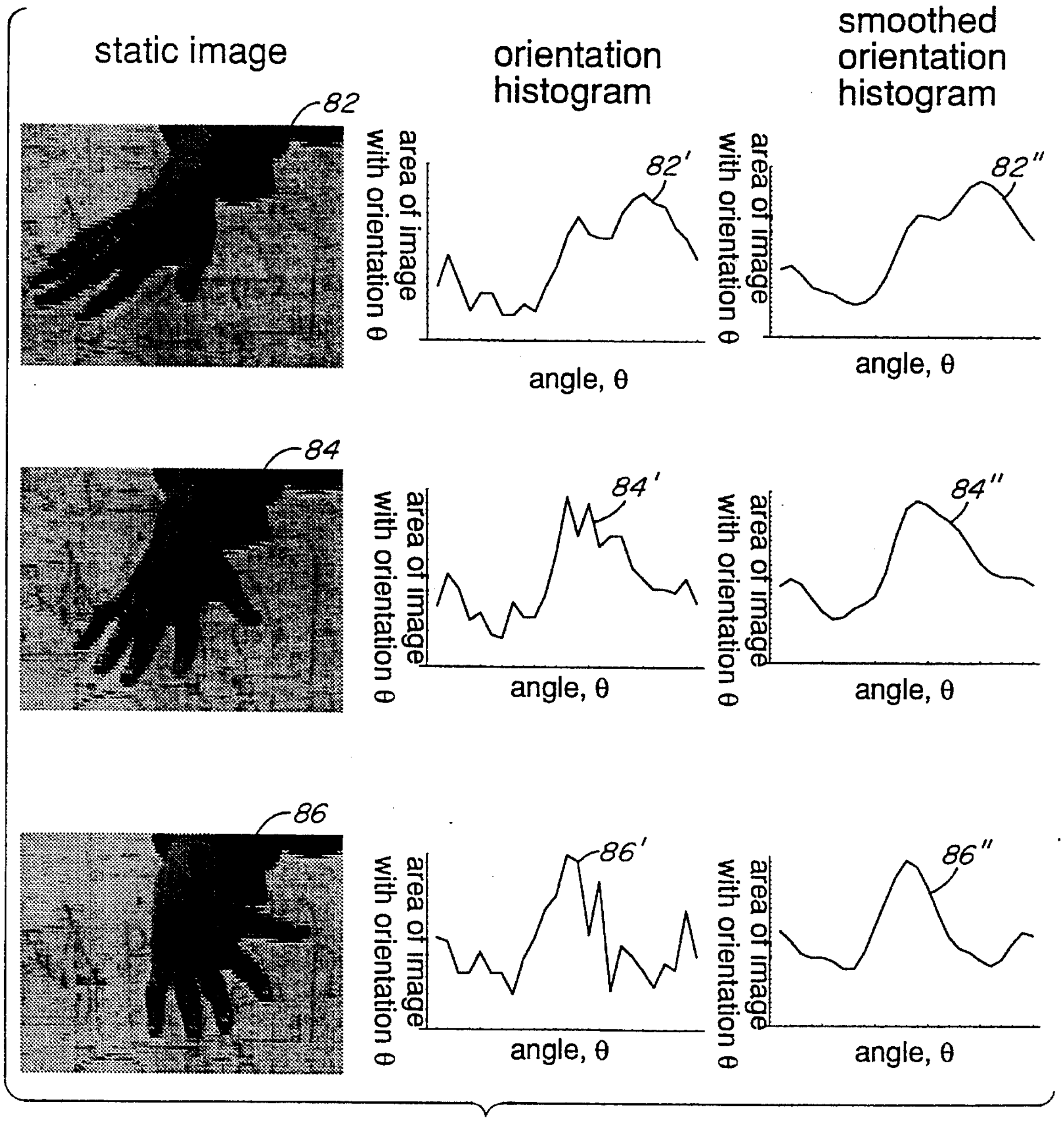
FIG. 4 is a diagrammatic, photographic and schematic illustration of the orientation histograms illustrated for various hand positions, showing the characteristic histogram signatures for both an unsmoothed and smoothed orientation histogram.

Referring now to FIG. 4, a series of digitized static images of a hand at different angles, namely images 82, 84 and 86 result in training histograms 82', 84' and 86'. The corresponding smooth histograms are illustrated at 82", 84" and 86".

Figure 5:
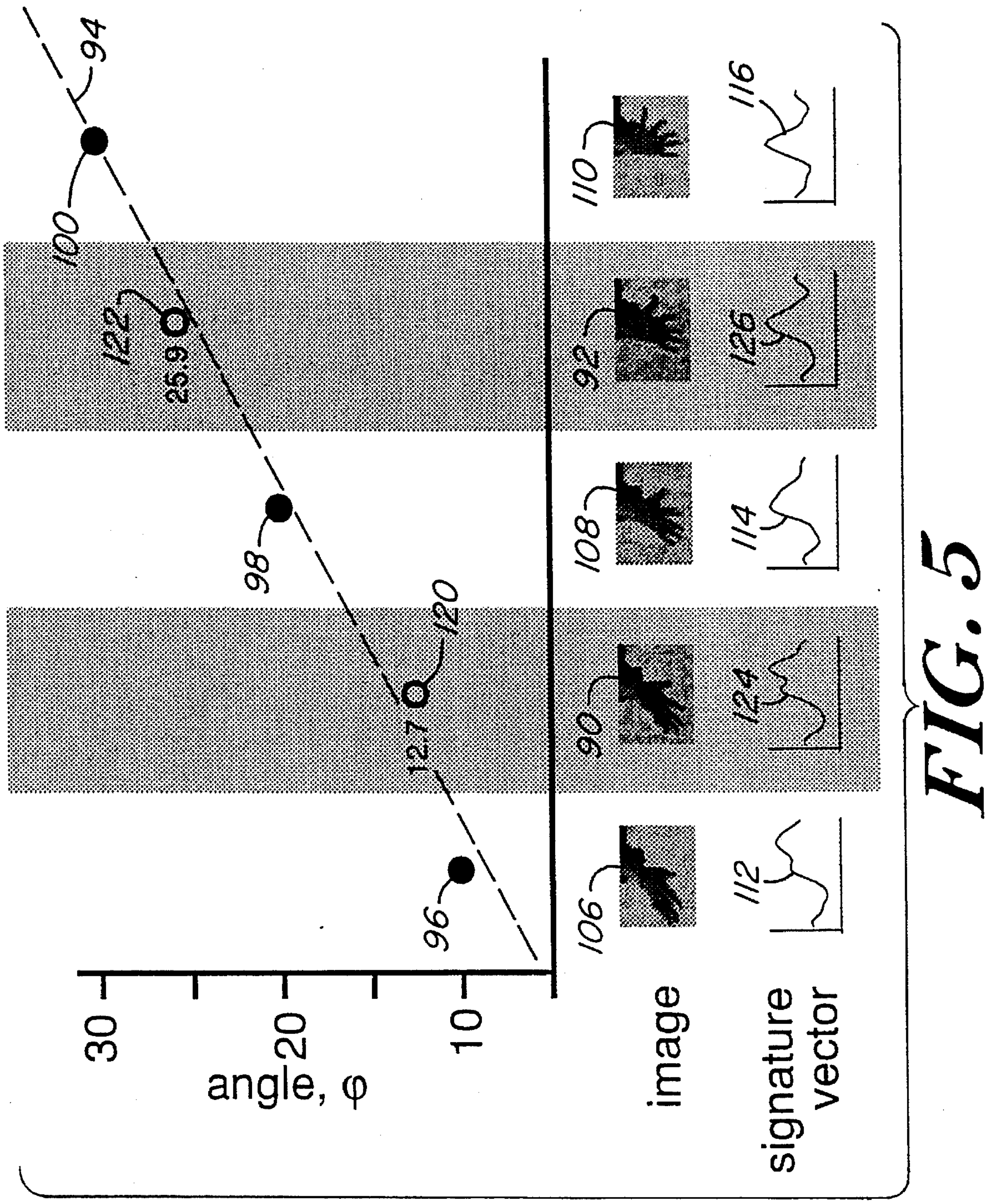
FIG. 5 is a diagrammatic representation of test results of the static gesture recognition algorithm associated with the detection system of FIG. 3, illustrating that detected hand orientations are in fact intermediate those of the preloaded training images; and, FIG. 6 is a block diagram illustrating the system utilized to provide a dymanic gesture histogram.

Referring now to FIG. 5, the results of utilizing the Subject System with static gestures illustrates that for intermediate hand positions 90 and 92, the detected angular response lies along a dotted line 94 which includes training points at 10° as illustrated by point 96, 20° as illustrated by point 98 and 30° as illustrated by point 100. The corresponding images and signature vectors are illustrated at corresponding points 106, 108 and 110, with the corresponding signature vectors at 112, 114 and 116.

As can be seen, dominent training image angles lie along a dotted line 94 corresponding to images 106, 108 and 110. These are the detected angles corresponding to the dominant position of the hands in these digitized images. The data points illustrated at 120 and 122 indicate detection of the dominant position through signatures 124 and 126, respectively, derived from the corresponding digitized image of the hand.

Note that for training images, the angular orientation of the hand was prespecified, whereas for test images the angular orientation was calculated by the subject algorithm presented herewith.

Figure 6:
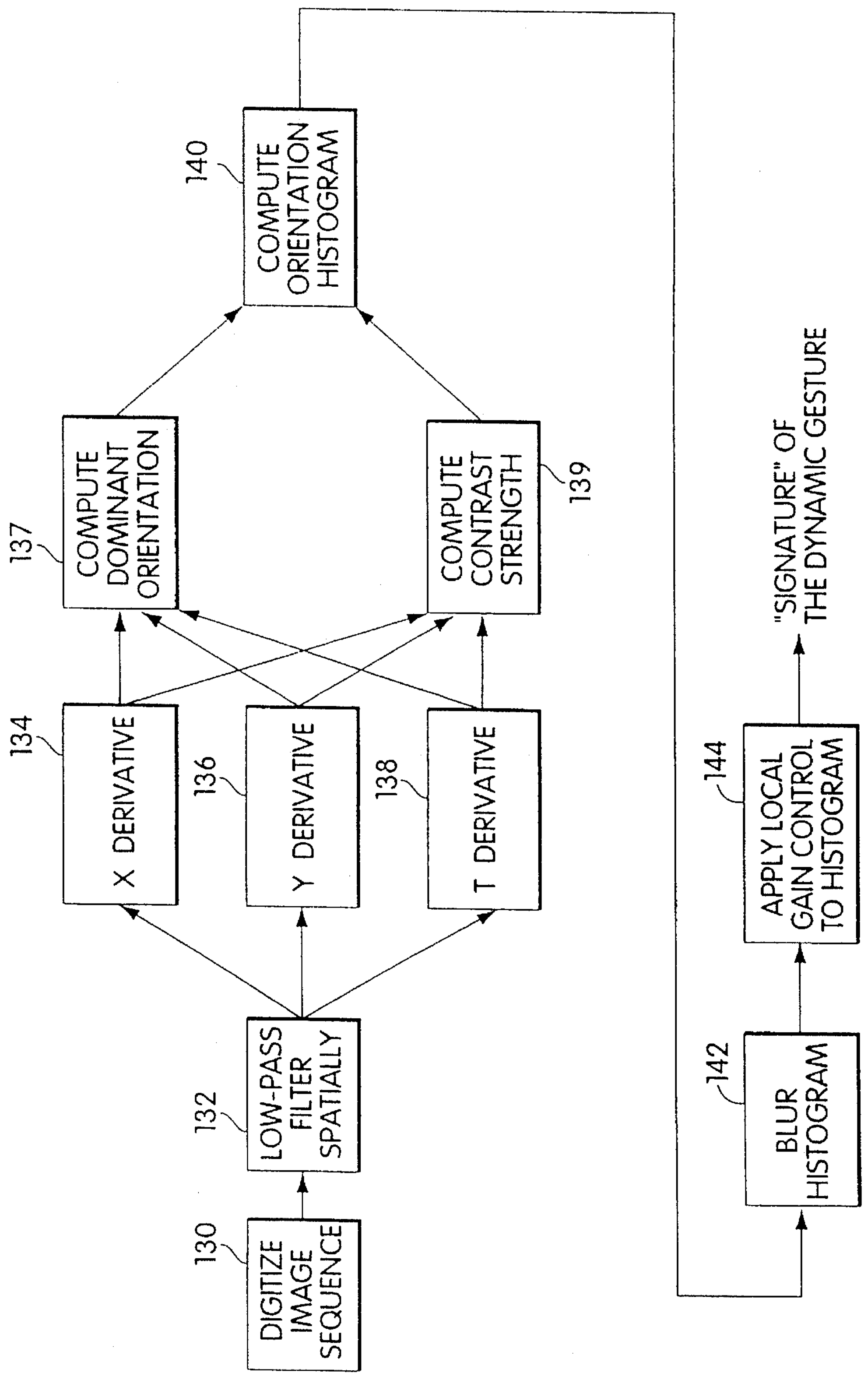

Referring now to FIG. 6, as mentioned hereinbefore, the dynamic gesture recognition system makes use of the same technique for determining gradients as described in connection with the static gesture recognition system. As can be seen from FIG. 6, the image is digitized to provide a digitized image sequence as illustrated at 130. This image is low pass spatially filtered as illustrated at 132 from whence x, y and t derivative generators, respectively, 134, 136 and 138 provide the derivatives with respect to the x, y and t directions corresponding to the 3-D map of FIG. 2B.

After having generated the 3-D map of FIG. 2B by virtue of the utilization of derivatives, unit 137 computes the dominant orientation, usually in terms of polar coordinates of the space-time intensity gradients associated with the moving gesture. The merge of the 3-D map into the 2-D histogram is accomplished at unit 140 which merges the 3-D map into the characteristic histogram as illustrated in 2C which provides for frequency of occurrence vs. both angular orientation and movement. The algorithm for doing the merge or conversion is given hereinafter. Note that means 139 are provided for computing contrast strength so as to be able to ignore image intensities below a preset threshhold.

Having generated the histogram which takes into account both orientation and movement as described above, the histogram may be blurred as illustrated at 142 to smooth the data. Again, local gain control may be applied to the histogram as illustrated at 144 to derive the characteristic signature for the dynamic gesture.

It will be appreciated that the system of FIG. 6 is utilized both in a training mode so as to derive 2-D template signatures against which signatures corresponding to incoming gestures are compared. Again, conventional interpolating techniques are utilized in the curve-matching or more specifically histogram-matching of the incoming histogram vs. those stored in a training sequence.

Note, in order to provide a characteristic signature or template for a dynamic gesture, this 3-D space-time-orientation map is converted into a 2-D space-time orientation histogram which graphs frequency of occurrence versus gesture angle and gesture movement by the following algorithm:

1) raster scan the (3-d) space-time-orientation map;
2) read-out the orientation of each vector;
3) go to the (2-d) histogram and add "1" to the count value stored at the orientation corresponding to this vector;
4) continue, from step 1, for the whole space-time-orientation map.

Spario-temporal orientation can be described in polar coordinates in the space-time orientation histogram, much like latitude and longitude coordinates in a map of the world. The longitude coordinate represents spatial orientation of the image information. The latitude coordinate represents the amount of motion in the direction of that spatial orientation. The "equator" or 0 degree latitude line represents zero motion, or stationary image information. The total number of counts along the 0 degree latitude line of the space-time orientation histogram indicates how much of the gesture was made of stationary image formation.

The 0 degree longitude line represents horizontally oriented image information. The number of counts of the 2-D space-time orientation histogram at the 0 degree longitude, 0 degree latitude position indicates how much of the gesture was composed of stationary, horizontally oriented image information. Higher latutude positions along the 0 degree longitude position indicate the amount of image information which was horizontally oriented, moving at some speed in the direction perpendicular to its horizontal spatial orientation, or vertically.

As to dynamic gesture recognition, in one test, a set of 16 gestures requiring hand movement was utilized as the histogram signature base. Such gestures included circular stirring motions by the hand; snapping of fingers; up, down, left, right gesturing for pointing purposes; hand motions to come closer and go away; waving goodbye; and a thumbs up hand gesture. In an initial test when utilizing the Subject space-time-orientation histogram for a given set of lighting conditions, 15 out of 16 different dynamic gestures were successfully recognized, whereas with different lighting conditions 10 out of 16 gestures were successfully recognized. While there was some degradation in performance under the different lighting condition, a relatively high recognition rate was maintained. It will be appreciated that because this gesture analysis is based on image orientation, which is robust to lighting changes, rather than image intensities, which can very strongly under different lighting conditions, a good amount of robustness to lighting conditions is maintained.

What is provided therefore is a system both for static gesture recognition and moving gesture recognition in which both systems utilize a histogram that constitutes a signature against which gestures are compared. The static gesture is a histogram of frequency of occurrence vs. orientation angle, whereas the moving dynamic gesture histogram utilizes spatial orientation information along with time information to generate a histogram reflective of not only angular orientation but also movement.

In summary, a low-level model-free dynamic and static hand gesture recognition system utilizes either a 1-D histogram of frequency of occurrence vs. spatial orientation angle for static gestures or a 2-D space-time orientation histogram for dynamic gestures. In each case the histogram constitutes the signature of the gesture which is used for gesture recognition. For moving gesture detection, a 3-D space-time orientation map is merged or converted into the 2-D space-time orientation histogram which graphs frequency of occurrence vs. both orientation and movement. It is against this representation or template that an incoming moving gesture is matched.

More specifically, the moving gesture is detected from the 3-D space-time orientation map merged into the two-dimensional frequency of occurrence vs. angle and movement histogram or template. The 2-D histogram or template is a plot of the frequency of occurrence of a given spatio-temporal orientation. This template is derived from the azimuthal and polar angle of the spatial-temporal gradient vector of the image intensities. The merge from the map to a 2-D space-time orientation histogram facilitates simple moving gesture recognition, with the merge effectively averaging gesture measurement and making the measurement independent of the actual time the gesture starts or stops and of the precise position at which the gesture occurs.

For static gesture analysis one starts with a spatial orientation map which is the result of taking a spatial intensity gradient that determines the dominant orientation and finding the orientation for each pixel in the image. Thereafter the characteristic histogram signature is generated. For dynamic gesture analysis one starts with a space-time orientation map, which is the result of taking the gradient of the space-time intensity data and finding spatio-temporal orientations for each pixel in the image. Afterwards the 2-D space-time orientation histogram or template is generated. In both the static and moving gesture embodiments, signatures are derived in a training sequence for a number of different hand positions and/or movements. Thereafter, a run time algorithm operates on a digitized version of the video hand image to detect hand angle and/or movement.

The program for accomplishing both static and dynamic gesture recognition is now presented.

```
(compile-load "/users/freeman/lisp/utility/functions-2.2.lisp")
(compile-load "/users/freeman/lisp/hands/static-aux.lisp")
(obv-require 'matrix)
(obv-require 'generic-fns)
(obv-require 'svd)

(setq filename "/users/freeman/images/hands/sh")
(setq image-max 5)


(load-image (format nil "~a~a" filename 1) :-> 'tmp)
;;; rescale it in the way that Michal will
(setq seq-list nil)
(dotimes (i image-max)
  (load-image (format nil "~a~a" filename (1+ i)) :-> 'tmp)
  (print (range tmp))
  (sub tmp (minimum tmp) :-> tmp)
  (print (range tmp))
  (mul tmp (/ 255.0 (maximum tmp)) :-> tmp)
  (print (range tmp))
  (print " ")
  (setq seq-list (append
                  seq-list
                  (list tmp))))
(make-image-sequence (list (nth 0 seq-list) (nth 2 seq-list) (nth 4 seq-list)) :-> 'train)
(make-image-sequence (list (nth 1 seq-list) (nth 3 seq-list)) :-> 'test)


;;; assumed angles of each of these training vectors.
;; ;;; this is from test.lisp
;; (setq theta.low 0.0 theta.high pi)
;; (setq del.theta (/ (- theta.high theta.low)
;;                  (1- train-max-really)))
;; (setq angle-list nil)
;; (dotimes (i train-max)
;;   (setq angle-list (append angle-list (list (+ theta.low (* i del.theta))))))
;; (print angle-list)
;;; july 9
(setq angle-list (list 10.0 20.0 30.0))

;; (setq histo-bins 36 strength-thresh-frac 25 blur t weighted-avg t)
;; (setq histo-bins 36 strength-thresh-frac 25 blur t weighted-avg nil)
(setq histo-bins 25 strength-thresh-frac 25 blur t weighted-avg t)
;;; make all the orientation histograms
(static-orientation-histogram train
                              :strength-thresh-frac strength-thresh-frac
                              :histo-bins histo-bins
                              :skip-border t
                              :debug nil
                              :blur blur
                              :-> 'train.ori)
(print-histo (frame 0 train.ori))
(print-histo (frame 1 train.ori))
(print-histo (frame 2 train.ori))
;;; find the average distance between them
(setq sigma (* 2 (get-average-dist train.ori)))   ;;; to compare with michal
(* 2 sigma sigma)
```

```
;;; (setq sigma (* 0.1 (get-average-dist train.ori)))
;;; (setq sigma (* 0.01 (get-average-dist train.ori)))
;;; (setq sigma (* 0.0001 (get-average-dist train.ori))) ;;; floating nan for weighted.
;;; make the matrix which we want to take the inverse of to find the RBF coefficients.
(setq arr (make-array
           (list (sequence-length train.ori) (sequence-length train.ori))
           :element-type 'single-float
           :initial-contents
           (progn
             (setq big-lis nil)
             (dotimes (j (sequence-length train.ori))
               (setq big-lis (append big-lis
                                     (list (progn
                                             (setq lis nil)
                                             (dotimes (i (sequence-length train.ori))
                                               (setq lis
                                                     (append lis
                                                             (list
                                                              (print (get-arr-coeff train.
ori sigma i j
                                                                                     :weigh
ted-avg weighted-avg))))))
                                             lis)))))
             big-lis)))
(print-values arr)
(setq inv (matrix-inverse arr))
(print-values inv)
(print-values (matrix-mul arr inv))

;;; get the interpolation function
(setq angle-data (make-array (length angle-list)
                             :element-type 'single-float
                             :initial-contents
                             angle-list))
(print-values angle-data)
;;; these are the coefficients for the interpolation function
(print-values (setq coeffs (matrix-mul inv (columnize angle-data))))

;;; now look at some of the output values.
(rbf-out (frame 0 train.ori) train.ori coeffs sigma :debug t :weighted-avg weighted-avg)
(rbf-out (frame 1 train.ori) train.ori coeffs sigma :debug t :weighted-avg weighted-avg)
(rbf-out (frame 2 train.ori) train.ori coeffs sigma :debug t :weighted-avg weighted-avg)


;;; read-in the test images, get their ori histograms, and test them.

;;; assumed angles of each of these testing vectors.
;; ;;; this is from test.lisp
;; (setq theta.low 0.0 theta.high (/ pi 10))
;; (setq del.theta (/ (- theta.high theta.low)
;;                 (1- test-max)))
;; (setq test-angle-list nil)
;; (dotimes (i test-max)
;;   (setq test-angle-list (append test-angle-list (list (+ theta.low (* i del.theta))))))
;; (print test-angle-list)
(setq test-angle-list (list 15.0 25.0))

;;; make all the orientation histograms
(static-orientation-histogram test
                              :strength-thresh-frac strength-thresh-frac
                              :histo-bins histo-bins
                              :blur blur
                              :-> 'test.ori)

(print-histo (frame 0 test.ori))
```

```
(dotimes (i test-max)
  (format t "index: ~a  actual angle: ~5f  interpolated angle: ~5f  diff: ~5f~%"
          i (nth i test-angle-list)
          (setq tmp (rbf-out (frame i test.ori) train.ori coeffs sigma :weighted-avg weigh
ted-avg))
          (setq diff (- (nth i test-angle-list) tmp)))
  (format t "error in degrees: ~5f ~%" (* diff (/ 180 pi))))
```

```
***************************************************************
static-aux.lisp    code to call and test static gesture recognition.

July 28, 1993  W. T. Freeman
***************************************************************

;;; static-aux.lisp  auxiiliary program for getting orientation histograms.


;;; simple filters
(make-filter '(0.0 1.0 -1.0)
             :-> 'dyc)

(make-filter '((0.0)
               (1.0)
               ( -1.0))
             :-> 'dxc)

;;; (1.0 6.0 15.0 20.0 15.0 6.0 1.0)
(make-filter '(1.0 4.0 6.0 4.0 1.0)
             :-> 'blur-1d)



;;; find orientation historgram for an image.  Don't do any blurring or agc, for now.
;;; For debug, set debug to (list y x) at the point you want to evaluate.
;;; To use the double-angle representation instead of ordinary angle, set double-angle to
t.
(defmethod static-orientation-histogram ((image image) &key
                                          (strength-thresh-frac 25)
                                          (histo-bins 25)
                                          (skip-border t)
                                          (debug-image nil)
                                          (debug nil)
                                          (blur nil)
                                          (double-angle nil)
                                          ->)
  (with-result ((result ->)
                (list :class 'image :dimensions (list 1 histo-bins) )
                'static-orientation-histogram image)
    (let ((y nil)
          (x nil))
      (if debug
          (format t "at y: ~a  x: ~a  image = ~a~%"
                  (setq y (car debug)) (setq x (cadr debug)) (round (iref image y x))))
      (with-local-viewables ((dxs (apply-filter dxc image))
                             (dys (apply-filter dyc image))
                             (pair (make-complex-image (list dys dxs)))
                             (phase (complex-phase pair))
                             (two (mul phase 2.0))
                             (strength (magnitude pair)))
      ;;; convert "two" to -pi to pi range
        (point-operation two #'(lambda (theta)
                                 (if (< theta (* -1.0 pi))
                                     (setq theta (+ theta (* 2 pi)))
                                     (if (> theta pi)
                                         (setq theta (- theta (* 2 pi)))
                                         theta)))
                         :binsize nil :-> two)
        (if debug-image (copy two :-> debug-image))
        (if debug
            (progn
              (format t "  dy: ~a  dx: ~a  angle: ~a  strength: ~a~%"
                      (iref dys y x)
                      (iref dxs y x)
                      (if double-angle
```

```
                    (iref two y x)
                    (iref phase y x))
                  (iref strength y x))))
        (get-histo (if double-angle
                       two
                       phase)
                   strength
                   :strength-thresh-frac strength-thresh-frac
                   :skip-border skip-border
                   :histo-bins histo-bins
                   :-> result)
        (if blur
          ;;; go to pains here to be sure to wrap-around properly.
            (progn
              (with-local-viewables ((big-histo (make-image (list (y-dim result)
                                                                   (* 3 (x-dim result)))))
                                     (tmp-histo (similar big-histo)))
                (paste result big-histo :y 0 :x 0 :-> big-histo)
                (paste result big-histo :y 0 :x (x-dim result) :-> big-histo)
                (paste result big-histo :y 0 :x (* 2 (x-dim result)) :-> big-histo)
                (apply-filter blur-1d big-histo :-> tmp-histo)
                (crop tmp-histo :y 0 :x (x-dim result) :y-dim 1 :x-dim (x-dim result) :->
result))))
        result))))


;;; an auxiliary program for static-orientation-histogram
;;; July 9, 1993  avoid counting in the border.
(defun get-histo (orientation strength
                              &key
                              (skip-border t)
                              (strength-thresh-frac 25.0)
                              (histo-bins 50)
                              -> )
  (with-result ((result ->)
                (list :class 'image :dimensions (list 1 histo-bins) )
                'static-orientation-histogram orientation strength)
    (zero! result)
    ;;; this is so the maximum strength isn't on the boundary.
    (with-local-viewables ((cropped-strength (if skip-border
                                                 (crop strength
                                                       :y 1
                                                       :x 1
                                                       :y-dim (- (car (dimensions strength
)) 2)
                                                       :x-dim (- (cadr (dimensions strengt
h)) 2))
                                                 strength)))
    (let* ((x-scale (/ histo-bins (* 2 pi)))
           (strength-thresh  (/ (maximum cropped-strength) strength-thresh-frac)))
      (format t "skip-border: ~a  (dimensions cropped-strength): ~a~%"
              skip-border (dimensions cropped-strength))
      (format t "strength-thresh-frac: ~a  (maximum cropped-strength): ~a  strength-thresh
: ~a~%"
              strength-thresh-frac (maximum cropped-strength) strength-thresh)
      (loop-over-image-positions
          ((tmp orientation)) (y x)
        (if (> (iref strength y x) strength-thresh)
            (if (or (not skip-border)
                    (not (border-pixel-p y x (dimensions orientation))))
                (progn
                  (setq x-out (round (- (* (+ pi (iref orientation y x)) x-scale) 0.5)))
                ;;; clip outputs to be within the histogram image size.
                ;;; (this should be a nop.)
                  (setq x-out (max 0 (min (1- histo-bins) x-out)))
                  (setf (iref result 0 x-out) (1+ (iref result 0 x-out)))))))))
```

```
    result)))

;;; return t if this is a border pixel.  nil if it is not.
(defun border-pixel-p (y x dims)
  (if (or (= y 0)
          (= x 0)
          (= y (1- (car dims)))
          (= x (1- (cadr dims))))
      t
      nil))

;;; method to apply this to image sequences.
(defmethod static-orientation-histogram ((seq image-sequence) &key
                                          (strength-thresh-frac 25)
                                          (histo-bins 25)
                                          (skip-border t)
                                          (debug-image nil)
                                          (debug nil)
                                          (blur nil)
                                          (double-angle nil)
                                          ->)
  (with-result ((result ->)
                (list :class 'image-sequence :dimensions (list 1 histo-bins) :length (sequ
ence-length seq))
                'static-orientation-histogram seq)
    (dotimes (i (sequence-length seq))
      (format t "forming orientation histogram ~a~%" i)
      (static-orientation-histogram (frame i seq)
                                    :strength-thresh-frac strength-thresh-frac
                                    :histo-bins histo-bins
                                    :skip-border skip-border
                                    :debug-image debug-image
                                    :debug debug
                                    :blur blur
                                    :double-angle double-angle
                                    :-> (frame i result)))
    result))

;;; find the average distance between all the orientation histogram vectors of a sequence.
(defun get-average-dist (ori-seq)
  (let ((total 0.0)
        (count 0.0)
        (histo-bins (cadr (dimensions ori-seq))))
    (dotimes (i (sequence-length ori-seq))
      (dotimes (j (sequence-length ori-seq))
        (if (not (= i j))
            (progn
              (setq count (1+ count))
              (setq total
                    (add total
                         (print (sqrt (* histo-bins (mean-square-error
                                                     (frame i ori-seq)
                                                     (frame j ori-seq))))))))))
    (print (/ total count))))

;;; ;;; test the above
;;; (setq total01 0.0 total12 0.0 total02 0.0)
;;; (dotimes (i 36)
;;;   (setq total01 (+ total01 (sqr (- (iref (frame 0 train.ori) 0 i)
;;;                                    (iref (frame 1 train.ori) 0 i)))))
;;;   (setq total12 (+ total12 (sqr (- (iref (frame 1 train.ori) 0 i)
;;;                                    (iref (frame 2 train.ori) 0 i)))))
;;;   (setq total02 (+ total02 (sqr (- (iref (frame 0 train.ori) 0 i)
;;;                                    (iref (frame 2 train.ori) 0 i)))))
;;;   )
;;; (/ (+ (sqrt total01) (sqrt total12) (sqrt total02)) 3.0)
```

```
;;; To initialize the matrix which you invert to get the RBF coefficients.
;;; Gives the i, jth coefficient of the matrix.
;;; Added weighted-avg mode,  see function rbf-out.
;;; Note that in weighted-avg mode, the order of the two coeffs, i and j, matters.
(defun get-arr-coeff (train.ori sigma i j &key (weighted-avg nil))
  (let* ((coeff   (exp (/ (* (cadr (dimensions train.ori))
                             (mean-square-error (frame i train.ori) (frame j train.ori)))
                          (* -2.0 (sqr sigma)))))
         (denom 0.0))
    (if weighted-avg
        (progn
          (dotimes (k (sequence-length train.ori))
            (setq denom (+ denom (get-arr-coeff train.ori sigma k j :weighted-avg nil))))
          (setq coeff (/ coeff denom))
          (format t "denom: ~a  coeff: ~a~%" denom coeff)
          ))
    coeff))


;;; function to give an angle out, from a radial basis function.
;;; July 7, 1993 added weighted-avg option.  This makes the rbf output
;;;  not be just a sum of the Gaussians.  But rather, a weighted average of the
;;;  training values, where the weighting is determined by the relative gaussian
;;;  altered distances.  Should make angle be monotonic, and treat out-of-training-set
;;;  values better.
(defun rbf-out (ori-in train.ori coeffs sigma &key (debug nil) (weighted-avg nil))
  (let ((count 0)
        (tmp 0.0)
        (denom 0.0)
        (total 0.0))
    (dolist (ori-training (image-list train.ori))
      (setq total (+ total (* (aref coeffs count 0)
                              (setq tmp (exp (/ (* (cadr (dimensions train.ori)) (mean-squ
are-error ori-in ori-training))
                                                (* -2.0 (sqr sigma))))))))
      (if weighted-avg
          (setq denom  (+ denom (exp (/ (* (cadr (dimensions train.ori))
                                           (mean-square-error ori-in ori-training))
                                        (* -2.0 (sqr sigma)))))))
      (if debug
          (format t "~5f  " tmp))
      (setq count (1+ count)))
    (if weighted-avg
        (setq total (/ total denom)))
    (if debug
        (format t "~%"))
    total))


(defun print-histo (histo)
  (dotimes (i (cadr (dimensions histo)))
    (format t "~a: ~5f~%" i (iref histo 0 i))))
```

```
******************************************************************
dynamic.lisp    code to call and test dynamic gesture recognition.

July 28, 1993  W. T. Freeman
******************************************************************

;;; dynamic.lisp  program to play with dynamic gesture recognition

;;; history:  Dec. 11, 1992  freeman created.
;;;           Dec. 15, 1992  tested out fft stuff.
;;; preprocessing on the 128x128 x 40 or so image sequences
;;; of the gestures:
;;; To make them and look at them in low res:
;;;
;;; smush allright.2.rle | avg4 | smush | avg4 | rlezoom 4 |getx11 -m
;;; to convert them all to obvius format:  see /u/freeman/images/convert.rle.to.dat.
;;;           Dec. 18, 1992  To do:  check out why the first thing that came to
;;;     mind didn't work out:  taking a squared difference of the fourier transform
;;;     magnitudes.   I tried to compare bye3 with the *1 test set. It liked down1
;;;     the best.  But same lighting, bye2, did work fine (tho not as deep a
;;;     an optimum as would like.  )  would principal components help that?  no.?
;;;           Dec. 21, 1992  do a thorough check of the squared difference brain-dead
;;;    method and of the squared difference of FFT magnitude a little-less-brain-dead
;;;    method.  Also, find a good 32 frame length cropping of all the gestures.
;;;           Dec. 28, 1992  try out space-time orientation analysis.
;;;           Dec. 29, 1992  Do a full comparison of the ori analysis version.
;;;            search for "dec. 29".
;;;           Jan. 3, 1993  restart after a bombing stop.
;;;           Jan. 5, 1993 reversed the order of blurring and agc for the h.train ones, de
c. 29 version.
;;;    I think this is all fine, except that it takes for freaking ever!!!  Speed up get-h
isto!!!
;;;    So far, I haven't run it yet for longer than 4 columns, and that was with the previ
ous mistake.
;;;         Jan. 8, 1993  hmm.  agc const of 10.0 now seems to be appropriate.  Why?
;;;         something to do with the resolution???  But a const of 1.0 just seems to be
;;;         accentuating too much noise.  Now, what about the other wierd stuff???
;;;         Ahh, it was just from not initializing the "result" image in the histograms.
;;;       Jan. 11, 1993  try again, after a bus error.

(progn
  (compile-load "/u/freeman/lisp/hands/dynamic-aux.lisp")
  (setq nframes 32)
  (setq dims (append (list nframes) '(32 32) ))

;;;Make temporary storage for the fft calculations
;;; initalize the complex valued arrays
  (setq array.3d.real (make-array dims :element-type 'single-float))
  (setq array.3d.imag (make-array dims :element-type 'single-float))
;;; make storage for images read-in
  (make-image-sequence '(32 32) :length 40 :-> 'input)
  (make-image-sequence '(32 32) :length 32 :-> 'test1)
  (make-image-sequence '(32 32) :length 32 :-> 'test2)
  (setq tmp32 (similar test1))


;;; make images in which to put the final comparison results.
  (make-image '(16 32) :-> 'pixel-compare)
  (make-image '(16 32) :-> 'mag-fft-compare)

;;; load-in all the training set iamges
  (setq file-list (list "allright1"      "comehere1"      "stirb1"        "right1"

                        "hi1"            "counter1"       "toodles1"      "bye1"

                        "snap1"          "left1"          "down1"         "up1"
```

```
                    "clock1"         "stira1"         "outta1"         "goback1"))
  (setq training-set (loop for name in file-list
                        collect
                        (sub-sequence
                         (load-image
                          (format nil "/u/freeman/images/hands/~a" name)) 0 32)))
;;; calculate the magnitudes of their dft's
  (setq mag-fft-training-set
        (loop for seq in training-set
              collect
              (magnitude-fft-sequence seq array.3d.real array.3d.imag)))


;;; load-in test sequences
  (setq test1-list (list "allright2"     "comehere2"     "stirb2"        "right2"

                         "hi2"           "counter2"      "toodles2"      "bye2"

                         "snap2"         "left2"         "down2"         "up2"
                         "clock2"        "stira2"        "outta2"        "goback2"))
  (setq test2-list (list "allright3"     "comehere3"     "stirb3"        "right3"

                         "hi3"           "counter3"      "toodles3"      "bye3"

                         "snap3"         "left3"         "down3"         "up3"
                         "clock3"        "stira3"        "outta3"        "goback3"))
  (dotimes (test (length test1-list))
    (load-image (format nil "/u/freeman/images/hands/~a"
                        (nth test test1-list)) :-> input)
    (sub-sequence input 0 32 :-> test1)
    (load-image (format nil "/u/freeman/images/hands/~a"
                        (nth test test2-list)) :-> input)
    (sub-sequence input 0 32 :-> test2)

;;; for each training image, find the distance to each test image:
    (dotimes (train (length training-set))
    ;;; first, the totally brain-dead comparison:  pixelwise squared error.
      (setq err1 (mean-square-error (nth train training-set) test1))
      (setq err2 (mean-square-error (nth train training-set) test2))
      (format t "pixelwise error.  same lighting: ~a   different lighting: ~a~%" err1 err2
)
      (setf (iref pixel-compare train test) err1)
      (setf (iref pixel-compare train (+ (length test1-list) test)) err2)

    ;;; next, the less brain-dead comparison:  magnitude dft squared error.
      (magnitude-fft-sequence test1 array.3d.real array.3d.imag :-> tmp32)
      (setq err1 (mean-square-error tmp32 (nth train mag-fft-training-set)))
      (magnitude-fft-sequence test2 array.3d.real array.3d.imag :-> tmp32)
      (setq err2 (mean-square-error tmp32 (nth train mag-fft-training-set)))
      (format t "mag fft error.  same lighting: ~a   different lighting: ~a~%" err1 err2)
      (setf (iref mag-fft-compare train test) err1)
      (setf (iref mag-fft-compare train (+ (length test1-list) test)) err2)))
  (save-image mag-fft-compare "/u/freeman/images/hands/mag-fft-compare")
  (save-image pixel-compare "/u/freeman/images/hands/pixel-compare"))


;;; compute percent correct

;;; to read the proper thing from the proper place
(defun get_distance (train test method lighting)
  (if (equal method "pixel")
      (if (equal lighting "same")
          (iref pixel-compare train test)
          (iref pixel-compare train (+ 16 test)))
      (if (equal lighting "same")
          (iref mag-fft-compare train test)
```

```
(iref mag-fft-compare train (+ 16 test)))))


(dolist (method (list "pixel" "fft-magnitude"))
  (dolist (lighting (list "same" "different"))
    (setq num_correct 0)
    (dotimes (test 16)
      (setq correct t)
      (dotimes (train 16)
        (if (< (get_distance train test method lighting)
               (get_distance test test method lighting))
            (setq correct nil)))
      (if correct
          (setq num_correct (1+ num_correct))))
    (format t "for ~a method and ~a lighting, were ~a correct, or ~a%~%"
            method lighting num_correct (* 100.0 (/ num_correct 16.0)))))

for pixel method and same lighting, were 5 correct, or 31.25%
for pixel method and different lighting, were 3 correct, or 18.75%

for fft-magnitude method and same lighting, were 15 correct, or 93.75%
for fft-magnitude method and different lighting, were 6 correct, or 37.5%

random chance:  6.25% correct.

;;;;;;;;;;;;;;;;;;;;;;;;;;;;;;;;;;;;;;;;;;;;;;;;;;;;;;;;;;;;;;;;;;;;;;;;;;;;;;;;;;;;;
;;;;;;;;;;;;;;;;;;;;;;;;;;;;;;;;;;;;;;;;;;;;;;;;;;;;;;;;;;;;;;;;;;;;;;;;;;;;;;;;;;;;;
;;;           Dec. 28, 1992  try out space-time orientation analysis.

(compile-load "/u/freeman/lisp/utility/functions-2.2.lisp")
(load-image (format nil "/u/freeman/images/hands/~a" "allright1") :-> 'test)

(progn
  (load-image (format nil "/u/freeman/images/hands/~a" "allright1"))
  (get-histo allright1 :-> 'allright1.h)
  (agc (blur allright1.h) :const 1.0 :-> 'allright1.agc)
  (load-image (format nil "/u/freeman/images/hands/~a" "allright2"))
  (get-histo allright2 :-> 'allright2.h)
  (agc (blur allright2.h) :const 1.0 :-> 'allright2.agc)
  (load-image (format nil "/u/freeman/images/hands/~a" "allright3"))
  (get-histo allright3 :-> 'allright3.h)
  (agc (blur allright3.h) :const 1.0 :-> 'allright3.agc))
(progn
  (load-image (format nil "/u/freeman/images/hands/~a" "comehere1"))
  (get-histo comehere1 :-> 'comehere1.h)
  (agc (blur comehere1.h) :const 1.0 :-> 'comehere1.agc)
  (load-image (format nil "/u/freeman/images/hands/~a" "comehere2"))
  (get-histo comehere2 :-> 'comehere2.h)
  (agc (blur comehere2.h) :const 1.0 :-> 'comehere2.agc)
  (load-image (format nil "/u/freeman/images/hands/~a" "comehere3"))
  (get-histo comehere3 :-> 'comehere3.h)
  (agc (blur comehere3.h) :const 1.0 :-> 'comehere3.agc)
  (load-image (format nil "/u/freeman/images/hands/~a" "hi1"))
  (get-histo hi1 :-> 'hi1.h)
  (agc (blur hi1.h) :const 1.0 :-> 'hi1.agc)
  (load-image (format nil "/u/freeman/images/hands/~a" "hi2"))
  (get-histo hi2 :-> 'hi2.h)
  (agc (blur hi2.h) :const 1.0 :-> 'hi2.agc)
  (load-image (format nil "/u/freeman/images/hands/~a" "hi3"))
  (get-histo hi3 :-> 'hi3.h)
  (agc (blur hi3.h) :const 1.0 :-> 'hi3.agc))

(progn
  (save-image allright1.h "/u/freeman/images/hands/allright1.h")
  (save-image allright2.h "/u/freeman/images/hands/allright2.h")
  (save-image allright3.h "/u/freeman/images/hands/allright3.h")
```

```
  (save-image comehere1.h "/u/freeman/images/hands/comehere1.h")
  (save-image comehere2.h "/u/freeman/images/hands/comehere2.h")
  (save-image comehere3.h "/u/freeman/images/hands/comehere3.h")
  (save-image hi1.h "/u/freeman/images/hands/hi1.h")
  (save-image hi2.h "/u/freeman/images/hands/hi2.h")
  (save-image hi3.h "/u/freeman/images/hands/hi3.h"))


(make-image '(3 6) :-> 'results.h.b1)
(make-image '(3 6) :-> 'results.h.b3)
(make-image '(3 6) :-> 'results.agc.b1)
(make-image '(3 6) :-> 'results.agc.b3)

(setq train-list (list allright1.h  comehere1.h hi1.h))
(setq test1-list (list allright2.h  comehere2.h hi2.h))
(setq test2-list (list allright3.h  comehere3.h hi3.h))


;;; compare all test images with all training images.
(dotimes (test (length test1-agc-list))
;;; for each training image, find the distance to each test image:
  (dotimes (train (length train-agc-list))
    ;;; non-agc'd
    (setf (iref res.h train test)
          (mean-square-error (nth test test1-list) (nth train train-list)))
    (setf (iref res.h train (+ (length test1-agc-list) test))
          (mean-square-error (nth test test2-list) (nth train train-list)))

    ;;; blur1
    (setf (iref res.h.b1 train test)
          (mean-square-error (blur (nth test test1-list)) (blur (nth train train-list))))
    (setf (iref res.h.b1 train (+ (length test1-agc-list) test))
          (mean-square-error (blur (nth test test2-list)) (blur (nth train train-list))))

    ;;; blur2
    (setf (iref res.h.b2 train test)
          (mean-square-error (blur  (nth test test1-list) :level 2 )
                             (blur  (nth train train-list) :level 2 )))
    (setf (iref res.h.b2 train (+ (length test1-agc-list) test))
          (mean-square-error (blur  (nth test test2-list) :level 2 )
                             (blur  (nth train train-list) :level 2 )))

    ;;; blur3
    (setf (iref res.h.b3 train test)
          (mean-square-error (blur  (nth test test1-list) :level 3 )
                             (blur  (nth train train-list) :level 3 )))
    (setf (iref res.h.b3 train (+ (length test1-agc-list) test))
          (mean-square-error (blur  (nth test test2-list) :level 3 )
                             (blur  (nth train train-list) :level 3 )))

    ;;; blur1, agc
    (setf (iref res.agc.b1 train test)
          (mean-square-error (agc (blur  (nth test test1-list) :level 1 ) :const 1.0)
                             (agc (blur  (nth train train-list) :level 1 ) :const 1.0)))
    (setf (iref res.agc.b1 train (+ (length test1-agc-list) test))
          (mean-square-error (agc (blur  (nth test test2-list) :level 1 ) :const 1.0)
                             (agc (blur  (nth train train-list) :level 1 ) :const 1.0)))

    ;;; blur2, agc
    (setf (iref res.agc.b2 train test)
          (mean-square-error (agc (blur  (nth test test1-list) :level 2 ) :const 1.0)
                             (agc (blur  (nth train train-list) :level 2 ) :const 1.0)))
    (setf (iref res.agc.b2 train (+ (length test1-agc-list) test))
          (mean-square-error (agc (blur  (nth test test2-list) :level 2 ) :const 1.0)
                             (agc (blur  (nth train train-list) :level 2 ) :const 1.0)))
```

```
    ;;; blur3, agc
    (setf (iref res.agc.b3 train test)
          (mean-square-error (agc (blur  (nth test test1-list) :level 3 ) :const 1.0)
                             (agc (blur  (nth train train-list) :level 3 ) :const 1.0)))
    (setf (iref res.agc.b3 train (+ (length test1-agc-list) test))
          (mean-square-error (agc (blur  (nth test test2-list) :level 3 ) :const 1.0)
                             (agc (blur  (nth train train-list) :level 3 ) :const 1.0))))


;;; lets look at these histograms
(agc (blur  (nth 0 test2-list) :level 3 ) :const 1.0 :-> 't2.0)
(agc (blur  (nth 0 test1-list) :level 3 ) :const 1.0 :-> 't1.0)
(agc (blur  (nth 0 train-list) :level 3 ) :const 1.0 :-> 'tr.0)

(agc (blur  (nth 1 test2-list) :level 3 ) :const 1.0 :-> 't2.1)
(agc (blur  (nth 1 test1-list) :level 3 ) :const 1.0 :-> 't1.1)
(agc (blur  (nth 1 train-list) :level 3 ) :const 1.0 :-> 'tr.1)

(agc (blur  (nth 2 test2-list) :level 3 ) :const 1.0 :-> 't2.2)
(agc (blur  (nth 2 test1-list) :level 3 ) :const 1.0 :-> 't1.2)
(agc (blur  (nth 2 train-list) :level 3 ) :const 1.0 :-> 'tr.2)

;;; save all this out, so that I can put these into my labnotebook.
(progn
  (save-image tr.0 "/u/freeman/images/hands/tmp/tr.0")
  (save-image t1.0 "/u/freeman/images/hands/tmp/t1.0")
  (save-image t2.0 "/u/freeman/images/hands/tmp/t2.0")
  (save-image tr.1 "/u/freeman/images/hands/tmp/tr.1")
  (save-image t1.1 "/u/freeman/images/hands/tmp/t1.1")
  (save-image t2.1 "/u/freeman/images/hands/tmp/t2.1")
  (save-image tr.2 "/u/freeman/images/hands/tmp/tr.2")
  (save-image t1.2 "/u/freeman/images/hands/tmp/t1.2")
  (save-image t2.2 "/u/freeman/images/hands/tmp/t2.2")
  (save-image results.h "/u/freeman/images/hands/tmp/results.h")
  (save-image results.h.b1 "/u/freeman/images/hands/tmp/results.h.b1")
  (save-image results.h.b2 "/u/freeman/images/hands/tmp/results.h.b2")
  (save-image results.h.b3 "/u/freeman/images/hands/tmp/results.h.b3")
  (save-image results.agc.b1 "/u/freeman/images/hands/tmp/results.agc.b1")
  (save-image results.agc.b2 "/u/freeman/images/hands/tmp/results.agc.b2")
  (save-image results.agc.b3 "/u/freeman/images/hands/tmp/results.agc.b3"))
```

```
****************************************************************
dynamic-aux.lisp    code to implement dynamic gesture recognition.

July 28, 1993  W. T. Freeman
****************************************************************

;;; dyanamic-aux.lisp  auxiliary programs for the dynamic gesture
;;;   recognition project.

;;; HIstory:  dec. 18, 1992 freeman created.
;;;           de. 28, 1992  freeman added two orientation histogramming functions.
;;;           Jan. 7, 1993  changed get orientation histo to try to speed it up.
;;;           Jan. 8, 1993  included a crucial "zero! result" line in get-ori...

;;; a magnitude method of a sequence of image pairs
(defmethod magnitude ((pair viewable-sequence) &key ->)
  (with-result ((result ->)
                (list :class 'image-sequence
                      :dimensions (dimensions pair) :length (sequence-length pair))
                'magnitude pair)
    (dotimes (i (sequence-length pair))
      (magnitude (frame i pair) :-> (frame i result)))
    result))


;;; Takes magnitude of Fourier transform of an image sequence.
;;; requires sequence dimensions be powers of two.
;;; requires the complex arrays, array.3d.real and array.3d.imag
;;;    to be created elsewhere.
(defun magnitude-fft-sequence (im-seq array.3d.real array.3d.imag &key ->)
  (with-result ((result ->) im-seq )
    (with-local-viewables ((dft (make-viewable-sequence
                                 (loop for i from 1 to (sequence-length im-seq)
                                       collect (make-complex-image (list (similar (frame 0
 im-seq))
                                                                         (similar (frame 0
 im-seq))))))))
      ;;; initialize the array elements
      (dotimes (i (sequence-length im-seq))
        (loop-over-image-positions ((rval (frame i im-seq))) (y x)
          (setf (aref array.3d.real i y x) rval))
        (loop-over-image-positions ((ival (frame i im-seq))) (y x)
          (setf (aref array.3d.imag i y x) 0.0)))
      ;;; take the dft
      (obvius::array-fft array.3d.real array.3d.imag)
      ;;; now convert this array back to an image sequence.
      ;;; (there must be some easier way to do the conversion.)
      (dotimes (i (sequence-length im-seq))
        (loop-over-image-positions ((rval (real-part (frame i dft)))) (y x)
          (setf rval (aref array.3d.real i y x)))
        (loop-over-image-positions ((ival (imaginary-part (frame i dft)))) (y x)
          (setf ival (aref array.3d.imag i y x))))
      (magnitude dft :-> result)
      (circular-shift result :y 16 :x 16 :-> result)
      result)))



;;;;;;;;;;;;;;;;;;;;;;;;;;;;;;;;;;;;;;;;;;;;;;;;;;;;;;;;;;;;;;;;;;;;;;;;;;
;;; dec. 28, 1992  orientation histogram stuff

(make-separable-filter '(0.0 1.0 0.0) '(0.0 1.0 0.0) :-> 'xy-filt)
(make-separable-filter '(0.0 1.0 -1.0) xy-filt :edge-handler ':dont-compute :-> 'dz-filt)
(make-separable-filter '(0.0 1.0 -1.0) '(1.0) :edge-handler ':dont-compute :-> 'dy-filt)
(make-separable-filter '(1.0) '(0.0 1.0 -1.0) :edge-handler ':dont-compute :-> 'dx-filt)
```

```
;;; takes as input the first derivatives of an image sequence (in x, y, z directions)
;;; and an image of the normalized magnitude of this gradient (~1.0 if
;;; above noise level;  ~0.0 if below noise level).  also input
;;; the desired dimensions of the histogram.
;;; Returns the histogram of the number of gradient vectors at that particular
;;; orientation.
;;;
(defun get-orientation-histo (dz-seq dy-seq dx-seq mag-seq  &key
                                       (ydim 100)
                                       (xdim 100)
                                       ->)
  (let ((x-histo nil)
        (y-histo nil))
    (with-result ((result ->)
                  (list :class 'image
                        :dimensions (list ydim xdim))
                  'get-orientation-histo dz-seq dy-seq dx-seq mag-seq)
      (zero! result)
      (dotimes (z (sequence-length dz-seq))
        (with-local-viewables ((tmp1 (square (frame z dx-seq)))
                               (tmp2 (square (frame z dy-seq)))
                               (pair (make-complex-image (list (frame z dy-seq)
                                                               (frame z dx-seq))))
                               (theta (complex-phase pair))
                               (phi (similar theta)))
          (add tmp1 tmp2 :-> tmp1)
          (square-root tmp1 :-> tmp1)
          (copy (frame z dz-seq) :-> (y-component pair))
          (copy tmp1 :-> (x-component pair))
          (complex-phase pair :-> phi)
          (loop-over-image-positions ((mag (frame z mag-seq))) (y x)
            (setq x-histo (min
                           (max
                            (floor (* xdim (/ (+ (iref theta y x) pi)
                                              (* 2 pi))))
                            0)

                           (1- xdim)))
            (setq y-histo (min
                           (max
                            (floor (* ydim (/ (+ (iref phi y x) (/ pi 2.0))
                                              pi)))
                            0)
                           (1- ydim)))
            (setf (iref result y-histo x-histo)
                  (+ mag (iref result y-histo x-histo))))))
      result)))


;;; make an image which shows how much every thing contributes to the
;;; orientation histogram.  Ie, at normal sized gradients, the value
;;; should be 1.0.  For really small gradients, the value should be 0.0.
(defun get-histo-mag (dx-seq dy-seq dz-seq const &key ->)
  (with-result ((result ->) dx-seq )
    (with-local-viewables ((tmp1 (square dx-seq))
                           (tmp2 (square dy-seq)))
      (add tmp1 tmp2 :-> tmp1)
      (square dz-seq :-> tmp2)
      (add tmp1 tmp2 :-> tmp1)
      (add tmp1 const :-> tmp2)
      (div tmp1 tmp2 :-> result))))
```

```
;;; for debugging the orientation histogram
(defun debug-ori-histogram (zdbg ydbg xdbg dz-seq dy-seq dx-seq mag-seq
                                  &key (ydim 100) (xdim 100))
  (let* ((dx (iref (frame zdbg dx-seq) ydbg xdbg))
         (dy (iref (frame zdbg dy-seq) ydbg xdbg))
         (dz (iref (frame zdbg dz-seq) ydbg xdbg))
         (mag (iref (frame zdbg mag-seq) ydbg xdbg))
         (theta (if (= dx dy 0.0)
                    0.0
                    (atan dy dx)))
         (phi (if (= dx dy dz 0.0)
                     0.0
                     (atan dz
                           (sqrt (+ (sqr dx) (sqr dy))))))
         (x-histo (min (floor (* xdim (/ (+ theta pi)
                                          (* 2 pi))))
                     (1- xdim)))
         (y-histo (min (floor (* ydim (/ (+ phi (/ pi 2.0))
                                              pi)))
                          (1- ydim))))
    (format t "at zdbg: ~a  ydbg: ~a  xdbg: ~a ~%" zdbg ydbg xdbg)
    (format t "dz: ~a  dy: ~a  dx: ~a   mag: ~a  ~%" dz dy dx mag)
    (format t "phi: ~a  theta: ~a~%" phi theta)
    (format t "y-histo position: ~a  x-histo position: ~a~%" y-histo x-histo)))


;;; get and debug orientation histogram
;;; After debugging, convert all these to with-local-viewables.
(defun get-histo (seq &key
                      (histo-mag-const 100.0)
                      (ydim 96) (xdim 96)
                      ->)
  (with-result ((result ->)
                (list :class 'image
                      :dimensions (list ydim xdim))
                'get-histo seq)
    (with-local-viewables ((dx-seq (apply-filter dx-filt seq))
                           (dy-seq (apply-filter dy-filt seq))
                           (dz-seq (apply-filter dz-filt seq))
    ;;; compute orientation histogram of the sequence "image"
                           (mag-seq (get-histo-mag dx-seq dy-seq dz-seq histo-mag-const)))
      (get-orientation-histo dz-seq dy-seq dx-seq mag-seq :ydim ydim :xdim xdim :-> result
)
      result)))
```

Having above indicated a preferred embodiment of the present invention, it will occur to those skilled in the art that modifications and alternatives can be practiced within the spirit of the invention. It is accordingly intended to define the scope of the invention only as indicated in the following claims.

What is claimed is:

1. A machine for detecting a dynamic gesture comprising:

means for providing a training histogram corresponding to a predetermined gesture;

means for generating a video image of a gesturing object;

means for generating a 3-D dynamic gesturing object map corresponding to said video image, points on said image of said dynamic gesturing object each having a local spario-temporal image orientation, said 3-D map including vectors graphing frequency of occurance vs. spatio-temporal orientation;

means for converting said 3-D map into a 2-D histogram graphing angular orientation of the vectors of said 3-D map against position:

means for comparing said histograms; and, means for indicating a match between said histograms, thereby to detect said gesture.

2. The machine of claim 1, wherein said histogram generating means includes means for taking the derivative of the intensity of the video image of said gesture with respect to two orthogonal directions.

3. The machine of claim 2, wherein said histogram generating means further includes means for taking the derivative of the intensity of the video image with respect to time.

4. The machine of claim 2, and further including means for taking the arc tangent of said derivatives to obtain the dominant angle of said video image.

5. The machine of claim 2, and further including means for taking the sum of the squares of said derivatives to provide a gradient strength measurement and means for rejecting from the generation of a histogram gradient strength below a predetermined threshhold.

6. The machine of claim 1, and further including means for blurring said histograms to provide a smooth histogram signature.

7. The machine of claim 1, and further including means for applying local gain control to said histograms.

* * * * *